United States Patent
Drobnis et al.

(10) Patent No.: US 11,975,136 B2
(45) Date of Patent: May 7, 2024

(54) SYSTEM AND METHOD FOR ASEPTIC COLLECTION OF MAMMALIAN AMNIOTIC FLUID

(71) Applicant: Hilltop BioSciences, Inc., Mansfield, MA (US)

(72) Inventors: Amanda Drobnis, Norton, MA (US); Terrell Suddarth, New Market, AL (US); Bruce Werber, Fort Lauderdale, FL (US); David Dutton, Amarillo, TX (US)

(73) Assignee: Hilltop BioSciences, Inc., Mansfield, MA (US)

(*) Notice: Subject to any disclaimer, the term of this patent is extended or adjusted under 35 U.S.C. 154(b) by 121 days.

(21) Appl. No.: 17/412,477

(22) Filed: Aug. 26, 2021

(65) Prior Publication Data
US 2022/0080101 A1    Mar. 17, 2022

Related U.S. Application Data

(60) Provisional application No. 63/078,510, filed on Sep. 15, 2020.

(51) Int. Cl.
*A61M 1/00*    (2006.01)

(52) U.S. Cl.
CPC ............ *A61M 1/87* (2021.05); *A61M 1/742* (2021.05); *A61M 1/76* (2021.05); *A61M 2202/0494* (2013.01)

(58) Field of Classification Search
CPC .......... A61M 1/87; A61M 1/742; A61M 1/76; A61M 2202/0494
See application file for complete search history.

(56) References Cited

U.S. PATENT DOCUMENTS

| | | | |
|---|---|---|---|
| 5,441,481 A * | 8/1995 | Mishra | A61B 5/145 600/581 |
| 8,308,657 B2 | 11/2012 | Park et al. | |
| 10,519,420 B2 | 12/2019 | Harrell | |
| 10,821,249 B2 * | 11/2020 | Vazales | A61M 25/10181 |
| 11,077,149 B1 | 8/2021 | Jones | |
| 2008/0124787 A1 * | 5/2008 | Christmann | G02B 21/32 435/285.1 |

(Continued)

*Primary Examiner* — Adam Marcetich
*Assistant Examiner* — Rachel O'Connell
(74) *Attorney, Agent, or Firm* — Daniel W. Roberts; Law Offices of Daniel W. Roberts, LLC

(57) ABSTRACT

A system for aseptic collection of mammalian amniotic fluid. The system includes a cannula having an attachment end and external end. The attachment end provides a concentric opening to a hollow chamber disposed about a central passage. The hollow chamber has a port disposed adjacent to the external end permitting at least a partial suction to be established within the hollow chamber, the attachment end thereby suctionally attached to a surface when the attachment end is disposed upon the surface. The central passage provides access to a central portion of the surface surrounded by the concentric opening of the hollow chamber. An extraction needle is disposed within the central passage of the cannula and presented to the central portion of the surface. The extraction needle penetrates the central portion of the surface and extracts amniotic fluid there beneath. An associated method of use is also provided.

39 Claims, 9 Drawing Sheets

(56) References Cited

U.S. PATENT DOCUMENTS

| | | | |
|---|---|---|---|
| 2011/0144571 A1* | 6/2011 | Ahluwalia | A61M 1/74 |
| | | | 604/30 |
| 2012/0029429 A1* | 2/2012 | Klein | A61M 5/172 |
| | | | 604/151 |
| 2014/0336600 A1* | 11/2014 | Harrell | C12N 5/0605 |
| | | | 435/325 |
| 2016/0030489 A1 | 2/2016 | Larsson et al. | |
| 2020/0077987 A1 | 3/2020 | Harrell | |
| 2020/0323197 A1* | 10/2020 | Tchirikov | A61M 1/3621 |
| 2020/0405976 A1* | 12/2020 | Patel | A61M 5/329 |

* cited by examiner

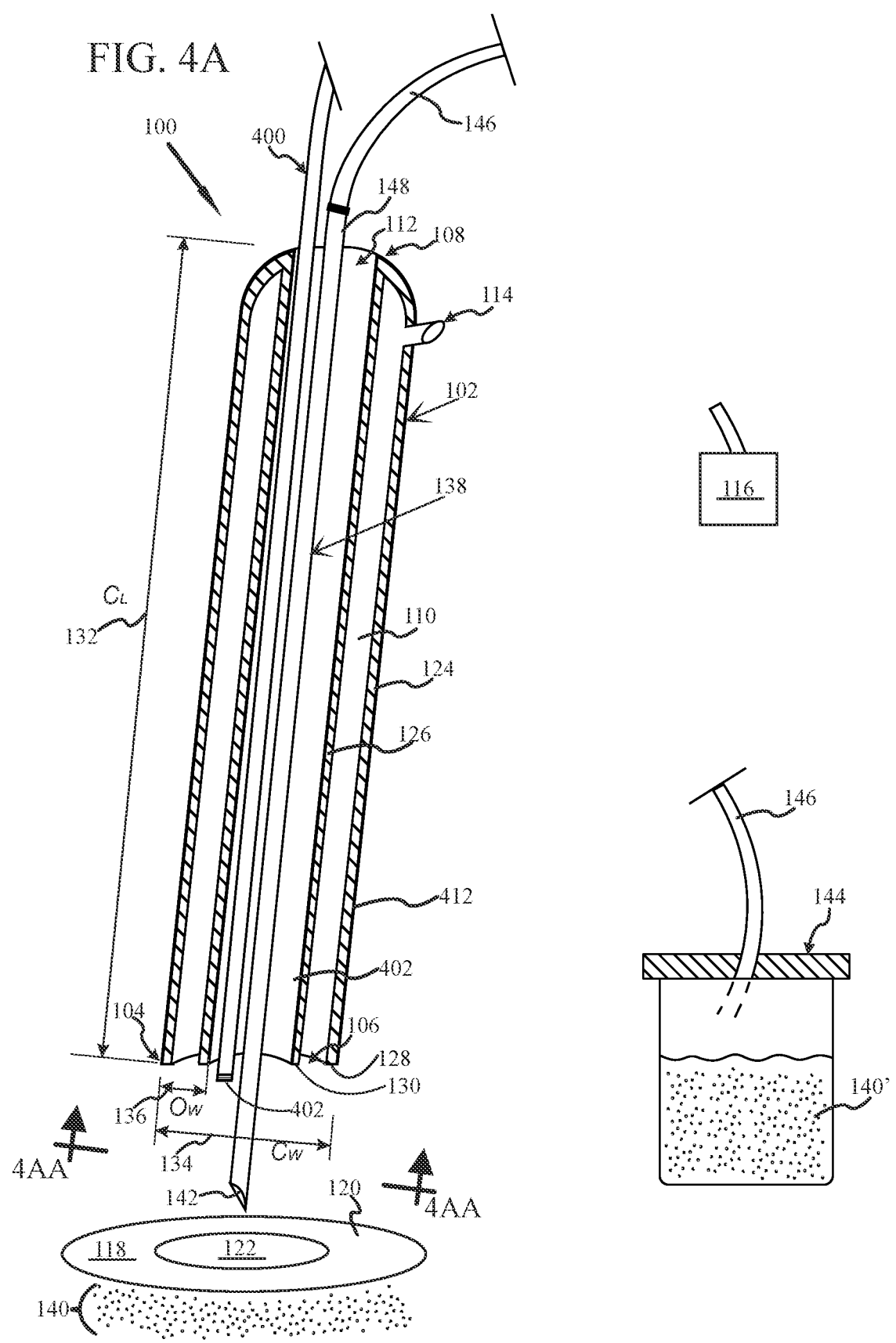

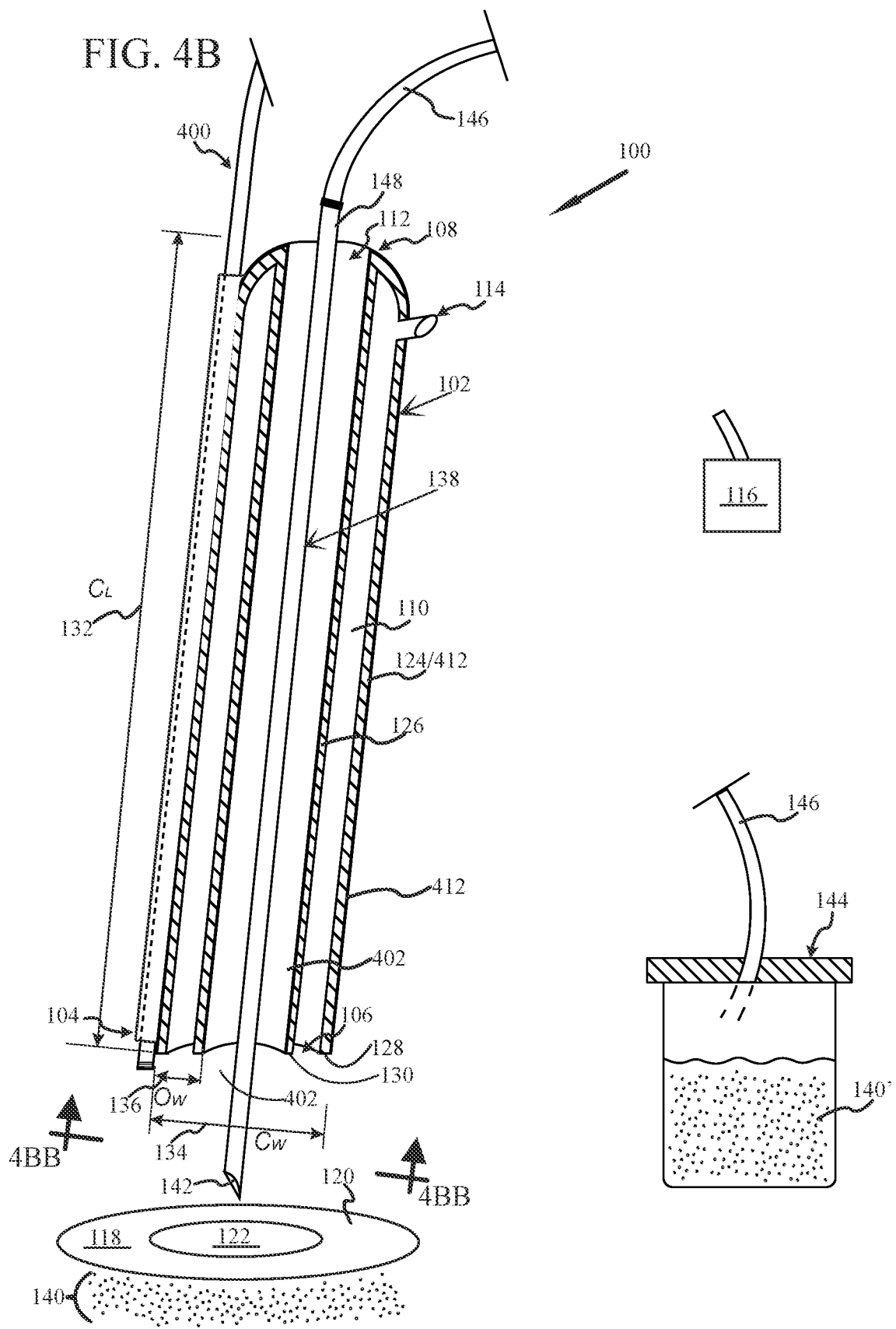

FIG. 5A
FIG. 5B
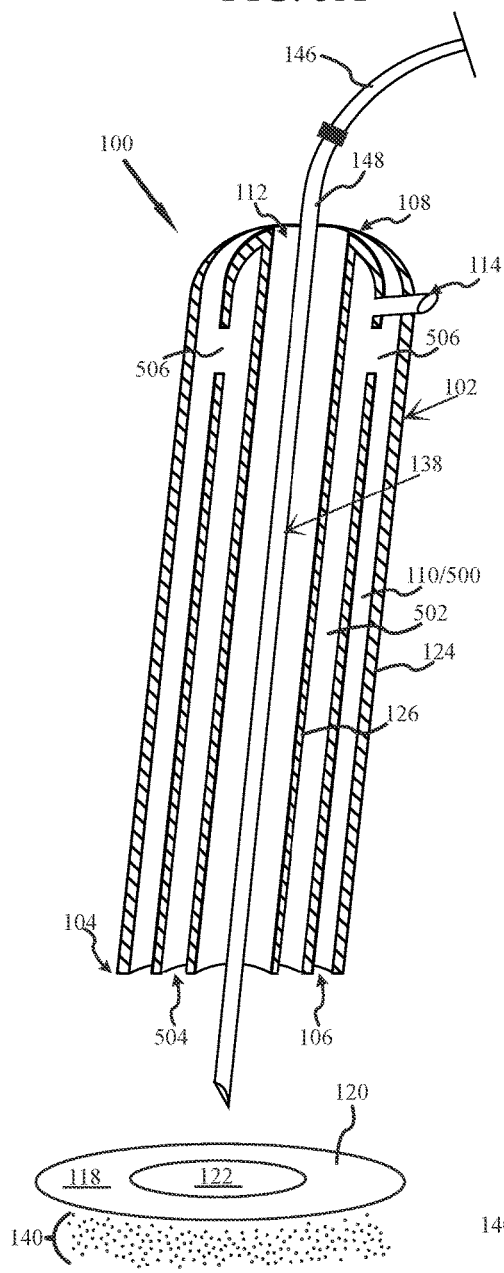
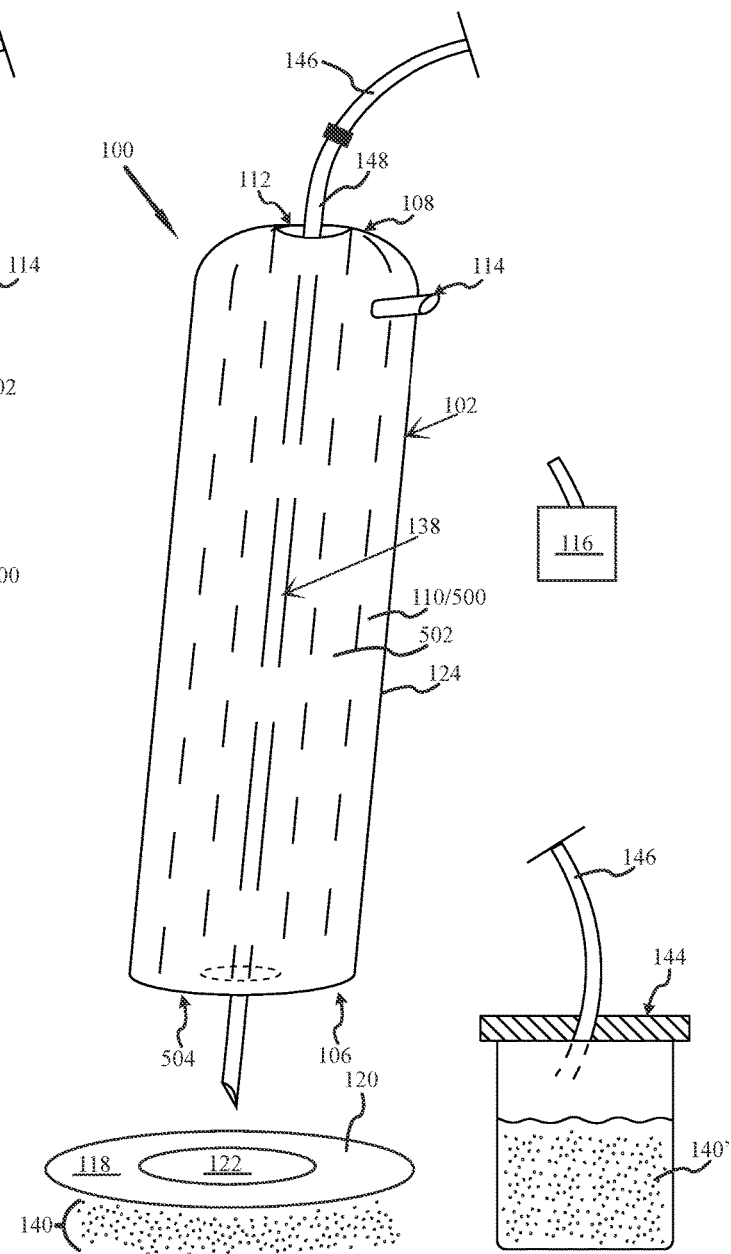

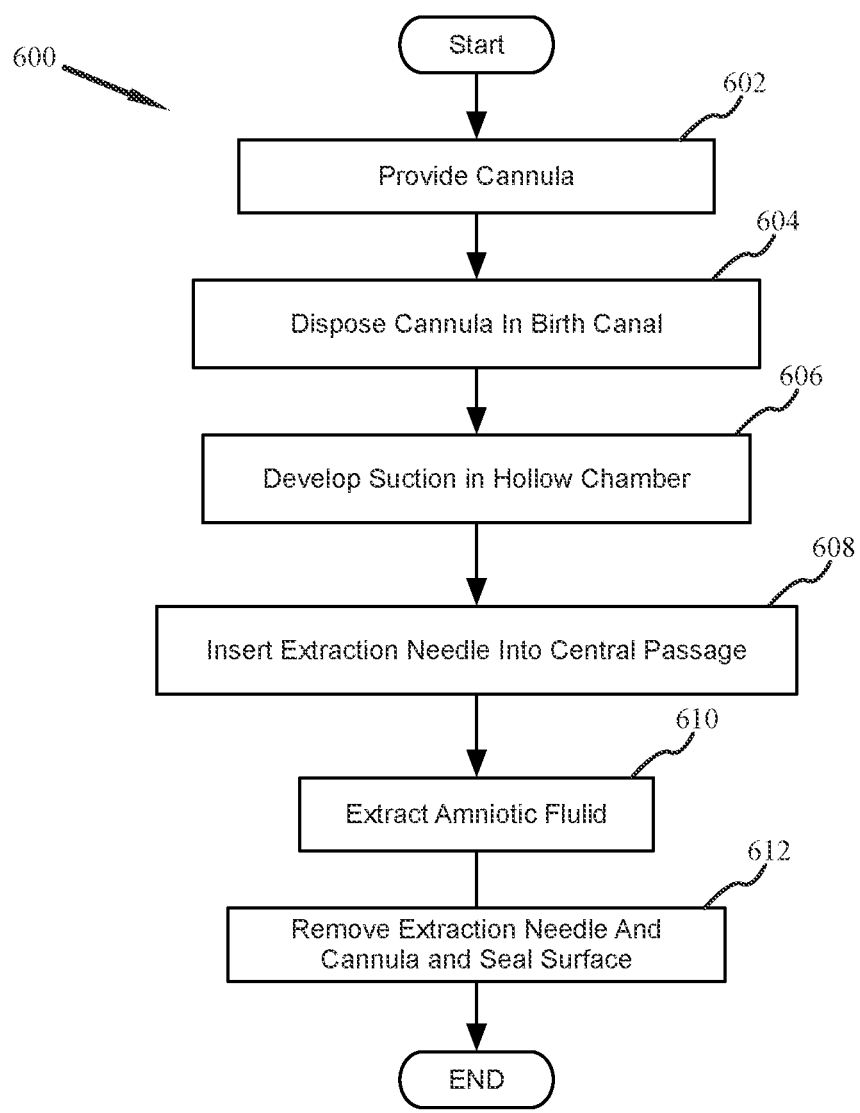

SYSTEM AND METHOD FOR ASEPTIC COLLECTION OF MAMMALIAN AMNIOTIC FLUID

CROSS REFERENCE TO RELATED APPLICATIONS

This application claims the benefit under 34 U.S.C. § 119(e) of U.S. Provisional Application No. 63/078,510 filed Sep. 15, 2021 and entitled SYSTEM AND METHOD FOR ASEPTIC COLLECTION OF MAMMALIAN AMNIOTIC FLUID, the disclosure of which is incorporated herein by reference.

FIELD OF THE INVENTION

The present invention relates generally to the aseptic collection of mammalian amniotic fluid prior to and during parturition. More specifically this provides a placental fluid recovery apparatus for the aseptic collection of amniotic fluid.

BACKGROUND

With a growing need for perinatal tissue based regenerative products in human and veterinary medicine, there is a growing need to aseptically collect the amniotic fluid via non-Cesarean and Cesarean delivery without risk to the mammal birthing or to the baby being birthed.

Current collection techniques are not aseptic and can pose risk to the end user of the amnion-based products if bacterial contamination is present.

Current collection techniques allow for other bodily fluid (i.e. urine, feces) to contaminate the amniotic fluid. More specifically, current collection techniques do not isolate the extraction area in any meaningful way. As such, the extraction site cannot be cleaned and/or sterilized, and such amniotic fluid collected is not received and maintained in a sterile process or environment. Even if the collected fluid is subsequently placed in a clean and/or sterile collection chamber, the likelihood of contamination is a precursor event.

Collection techniques currently in use are seldom able to collect all or even most of the amniotic fluid containing important proteins that could be lost. As such, the efficiency of current extraction processes are far below desired levels and the cost per unit of amniotic fluid collected is disproportionately higher than it would be if extraction methods and systems were more efficient.

Hence there is a need for a method and system that is capable of overcoming one or more of the above identified challenges.

SUMMARY OF THE INVENTION

Our invention solves the problems of the prior art by providing novel systems and methods for aseptically collecting the amniotic fluid with a placental fluid recovery apparatus that can be aseptically presented during birth and uses suction or inherent pressure from the amniotic sack to collect the amniotic fluid.

In particular, and by way of example only, according to at least one embodiment, provided is a system for aseptic collection of mammalian amniotic fluid, including: a cannula having an attachment end and external end, the attachment end providing a concentric opening to a hollow chamber disposed about a central passage, the hollow chamber having a port disposed adjacent to the external end, the port structured and arranged to permit at least a partial suction to be established within the hollow chamber, the attachment end thereby suctionally attached to a surface when the attachment end is disposed upon the surface; the central passage providing access to a central portion of the surface surrounded by the concentric opening of the hollow chamber; and an extraction needle to be disposed within the central passage of the cannula and presented to the central portion of the surface, the extraction needle structured and arranged to puncture the central portion of the surface and extract amniotic fluid there beneath.

For yet another embodiment, provided is a system for aseptic collection of mammalian amniotic fluid, including: a cannula having an attachment end and opposite thereto an external end with a central passage passing therebetween; a first hollow chamber disposed about the central passage and providing a first concentric opening proximate to the attachment end; a second hollow chamber disposed about the first hollow chamber and providing a second concentric opening proximate to the attachment end; at least one vent between the first hollow chamber and the second hollow chamber; a suction port disposed in an outer wall of the cannula proximate to the external end, the suction port in communication with the second hollow chamber and structured and arranged to permit at least a partial suction to be established within the first hollow chamber and the second hollow chamber, the attachment end thereby suctionally attached to a surface when the attachment end is disposed upon the surface.

Still, for yet another embodiment, provided is a system for aseptic collection of mammalian amniotic fluid, including: a cannula having a double wall defining a hollow chamber about a central passage, the cannula having an attachment end and an external end, the double wall further defining a concentric opening about the central passage at the attachment end; a port disposed adjacent to the external end, the port structured and arranged to permit at least a partial suction to be established within the hollow chamber, the attachment end thereby suctionally attached to a surface when the attachment end is disposed upon the surface; the central passage providing access to a central portion of the surface surrounded by the concentric opening of the hollow chamber; and an extraction needle to be disposed within the central passage of the cannula and presented to the central portion of the surface, the extraction needle structured and arranged to puncture the central portion of the surface and extract amniotic fluid there beneath.

Further still, for yet another embodiment, provided is a method for aseptic collection of mammalian amniotic fluid of a pregnant mammal having a birth canal, including: providing a cannula, the cannula having; an attachment end and external end, the attachment end providing at least one concentric opening to at least one hollow chamber disposed about a central passage, the at least one hollow chamber having a port disposed adjacent to the external end, the port structured and arranged to permit at least a partial suction to be established within the at least one hollow chamber, the attachment end thereby suctionally attached to a tissue surface when the attachment end is disposed upon the tissue surface; the central passage providing access to a central portion of the tissue surface surrounded by the concentric opening of the hollow chamber; and an extraction needle to be disposed within the central passage of the cannula and presented to the central portion of the tissue surface, the extraction needle structured and arranged to puncture the central portion of the tissue surface and extract amniotic fluid there beneath; disposing the attachment end of the cannula through the birth canal to seat upon a tissue surface within the pregnant mammal; developing a suction within the at least one hollow chamber, the suction drawing at least a portion of the tissue surface into the at least one concentric opening of the at least one hollow chamber to temporarily attach and seal the at least one concentric opening to the tissue surface; disposing the extraction needle through the central passage of the cannula and through central portion of the tissue surface; extracting amniotic fluid from below the central portion of the tissue surface through the extraction needle; and removing the extraction needle.

BRIEF DESCRIPTION OF THE DRAWINGS

FIG. 4AA is an end view of the attachment end of the system for aseptic collection of mammalian amniotic fluid shown in FIG. 4A in accordance with at least one embodiment of the present invention;

FIG. 4BB is an end view of the attachment end of the system for aseptic collection of mammalian amniotic fluid shown in FIG. 4B in accordance with at least one embodiment of the present invention;

FIGS. 5A and 5B conceptually illustrate a longitudinal cut through and external view of an alternative system for aseptic collection of mammalian amniotic fluid in accordance with at least one embodiment of the present invention; and FIG. 6 presents a high-level flow diagram for a method of collecting mammalian amniotic fluid in accordance with at least one embodiment of the present invention.

DETAILED DESCRIPTION

Figure 1:
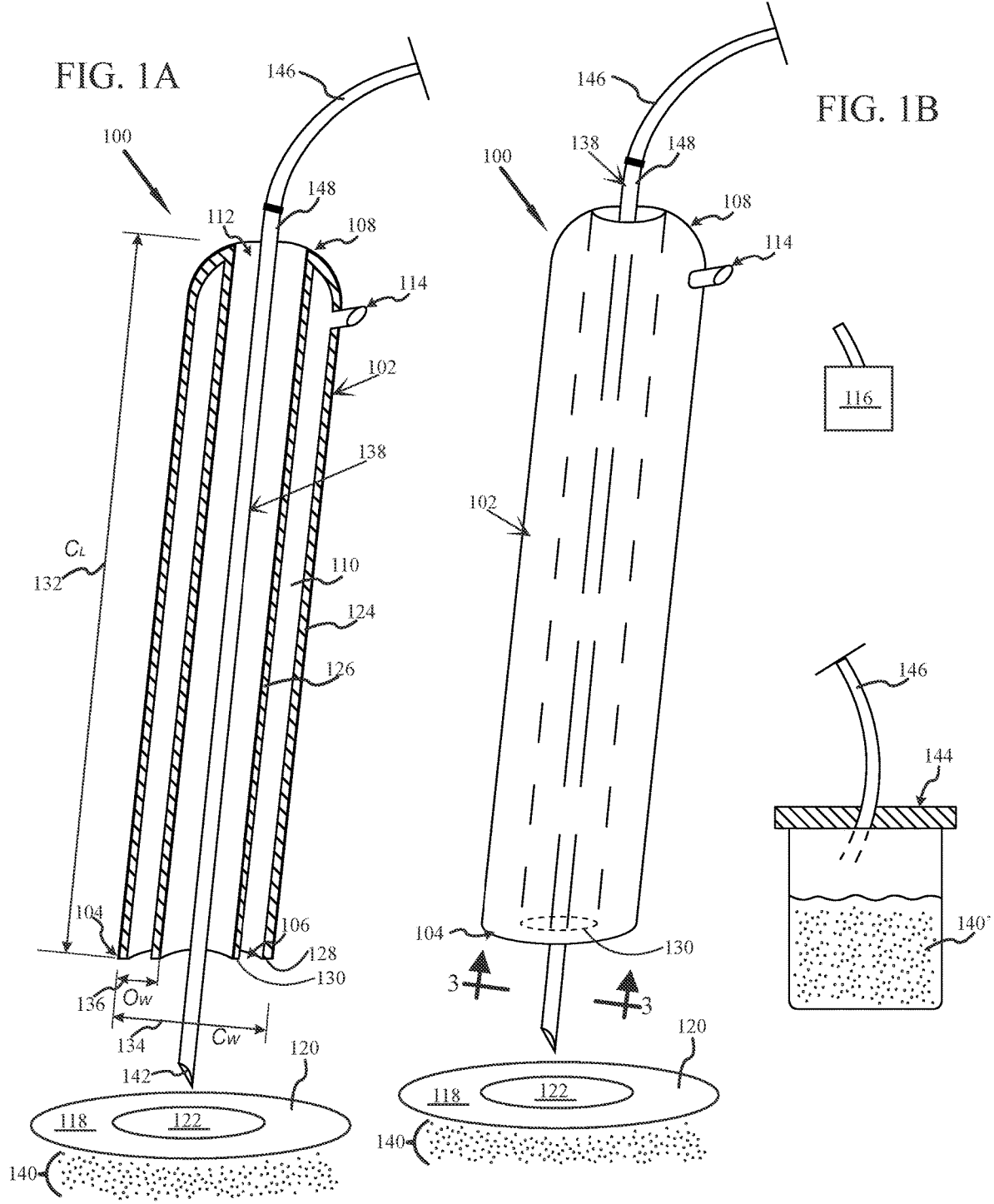
FIGS. 1A and 1B conceptually illustrate a longitudinal cut through and external view of a system for aseptic collection of mammalian amniotic fluid in accordance with at least one embodiment of the present invention.

Before proceeding with the detailed description, it is to be appreciated that the present teaching is by way of example only, not by limitation. The concepts herein are not limited to use or application with a specific system or method for aseptic collection of amniotic fluid. Thus, although the instrumentalities described herein are for the convenience of explanation shown and described with respect to exemplary embodiments, it will be understood and appreciated that the principles herein may be applied equally in other types of systems and methods involving aseptic collection of amniotic fluid.

This invention is described with respect to preferred embodiments in the following description with references to the Figures, in which like numbers represent the same or similar elements. It will be appreciated that the leading values identify the Figure in which the element is first identified and described, e.g., element 100 first appears in FIG. 1.

Turning now to the figures, and more specifically FIGS. 1A and 1B, there is shown a System For Aseptic Collection of Amniotic Fluid 100, hereinafter SFACAF 100, in accordance with at least one embodiment of the present invention. As will be more fully described below, SFACAF 100 incorporates an advantageous and unique cannula 102.

Moreover, an embodiment of SFACAF 100 is shown conceptually with a longitudinal cut through side view (FIG. 1A) and a corresponding external side view (FIG. 1B) of cannula 102. More specifically, cannula 102 is appreciated to have an attachment end 104 and opposite thereto an external end 108. The attachment end 104 provides a concentric opening 106 to a hollow chamber 110 disposed about a central passage 112 extending from the attachment end 104 to the external end 108.

At least one port 114 is disposed adjacent to the external end 108 of the cannula 102, the port structured and arranged for attachment to a suction system 116, the port thereby structured and arranged to permit at least a partial suction to be established within the hollow chamber 110 about the central passage 112. This partial suction within the hollow chamber 110 thereby permits the cannula 102 to be suctionally attached (e.g., attached by suction) to a surface 118 when the attachment end 104 is disposed upon the surface 118. For at least one embodiment the surface 118 is an amnionic membrane 120.

When such a suctional attachment between the attachment end 104 and the surface 118 is established, it will be appreciated that the central passage 112 permits access to a central portion 122 of the surface 118. It will be understood and appreciated that the central portion 122 of the surface 118 is not necessarily the center of the surface in general, but rather is the central portion 122 of the surface 118 relative to the position of the attachment end 104 of the cannula 102.

With respect to at least FIG. 1A, it will be appreciated that for at least one embodiment, the cannula 102 is at least a double walled structure defining a hollow chamber 110 about a central passage 112. More specifically, there is an outer wall 124 and an inner wall 126 with the outer wall 124 and the inner wall 126 joining proximate to the external end 108 as a sealed end of the hollow chamber 110 with the concentric opening 106 defined by the respective distal end 128 of the outer wall and distal end 130 of the inner wall 126 at the attachment end 104. For at least one embodiment the hollow chamber 110 is appreciated to be a substantially cylindrical hollow chamber. However, it will be understood and appreciated that for varying embodiments, the outer wall 124 and the inner wall 126 may have a variety of cross-sectional geometries such that the hollow chamber may be non-cylindrical, and potentially even not generally an oval, indeed hexagonal, pentagonal, or other geometries are within the scope of the present teaching, though it is realized that circular or at least substantially circular may be the most economical to fabricate. More specifically, regardless of cross-sectional geometry, a principle teaching of the present invention is that the hollow chamber 110 is structured and arranged to provide a suction cavity of the cannula 102.

The inner wall 126 may also be appreciated to define the central passage 112, which for at least one embodiment is a substantially cylindrical passage, though again, in varying embodiments the cross section of the central passage 112 need not be circular or even oval to still remain within the teachings of the present application.

It may further be appreciated that for at least one embodiment the distal ends 128 and 130 of the outer wall 124 and inner wall 126 are rounded so as not to provide a sharp or abrupt point of contact to the surface 118. Further, for at least one embodiment the distal ends 128 and 130 may be flared out as an inverted mushroom, again to provide a smooth contacting area to be disposed upon the surface 118. Further still, for at least one embodiment the distal ends 128 and 130 may be coated with a material such as silicon, rubber, or other semi pliable material to further facilitate the suctional attachment of the attachment end 104 to the surface 118 with minimized abrasion or trauma to the surface 118.

As the surface 118 is generally understood and appreciated to be mammalian tissue, such as the amnion, it will be also understood and appreciated that this surface 118 is flexible, and very likely exhibits some degree of elasticity. When the attachment end is disposed upon the surface 118 and a partial suction created within the hollow chamber 110, the surface 118 disposed below the concentric opening 106 will be drawn up against the attachment end, and in many cases may even be drawn partially into the concentric opening 106.

As such, it will be appreciated that the tissues comprising the surface 118 and the attachment end 104 collectively interact to provide and achieve at least a temporary seal between the attachment end 104 and the surface 118. As the cannula 102 extends away from the surface to the external end 108, which is appreciated to be external to the animal from which the amniotic fluid is to be extracted, it will be understood and appreciated that the central passage 112 provides direct access to the central portion 122 of the surface 118, which is effectively isolated from the rest of the surface 118, tissues, and fluids of the animal.

This permits the central portion 122 to be cleaned, such as by flushing with sterile water, sterile saline, antibiotics, the application of UV light, or such other material or process as felt most appropriate for the given situation. Moreover, the central portion 122 may be effectively isolated from both the tissues and fluids of the mother animal, but also the general environment. Such ability to clean and/or sterilize the central portion 122 advantageously improves the quality of the fluid to be extracted, as well as reducing the potential possibility of introducing foreign materials or infection causing materials that could harm either the mother animal or the developing fetus.

With respect to the issue of sterility, it will be understood and appreciated that for at least one embodiment the cannula 102, is formed from a material that is sterilized before use, and/or hermetically sealed to preserve the sterile condition prior to opening of the packaging for use as discussed herein. It will also be understood and appreciated that for at least one embodiment the cannula 102 is intended for single use, and yet for another embodiment the cannula 102 may be re-sterilized and re-used. For at least one embodiment, the cannula 102 is made of metal, such as stainless steel. For yet another embodiment the cannula is made from plastic, polycarbonate, ceramic, or other non-metallic materials.

To achieve such advantageous access to the central portion 122 of the surface 118, for at least one embedment the cannula 102 has a length $C_L$ 132 of about 12 to 24 inches, e.g., about 30 to 60 centimeters. For at least one embedment the cannula 102 has a width $C_W$ 134 of about 1 to 2 inches, e.g., about 2.5 to 5 centimeters. The concentric opening of the cannula 102 may have a width 136 of about 0.125 to 0.5 inch, e.g., about 0.3175 to 1.27 centimeters. From these potential measurements, it will be understood and appreciated that for a cylindrical embodiment, the central passage 112 may have a width of about 0.875 to 1.875 inch, e.g., about 2.2225 to 4.7625 centimeters.

SFACAF 100 further includes a second cannula which may be referred to as an extraction needle 138. It will be understood and appreciated that the extraction needle 138 is to be disposed within the central passage 112 of the cannula 102 and presented to the central portion 122 of the surface 118. The extraction needle 138 is structured and arranged to penetrate/puncture/cut the central portion 122 of the surface 118 and extract the amniotic fluid 140 there beneath. Moreover, the extraction needle 138 is hollow, having an internal passage 142 through which amniotic fluid 140 may be drawn or delivered.

The extracted amniotic fluid 140' extracted by the extraction needle 138 is delivered to a fluid reservoir 144 in fluid communication with the extraction needle 138. Typically, such fluid communication with the extraction needle 138 is achieved with flexible tubing 146 coupled to the external end 148 of the extraction needle 138.

Figure 2:
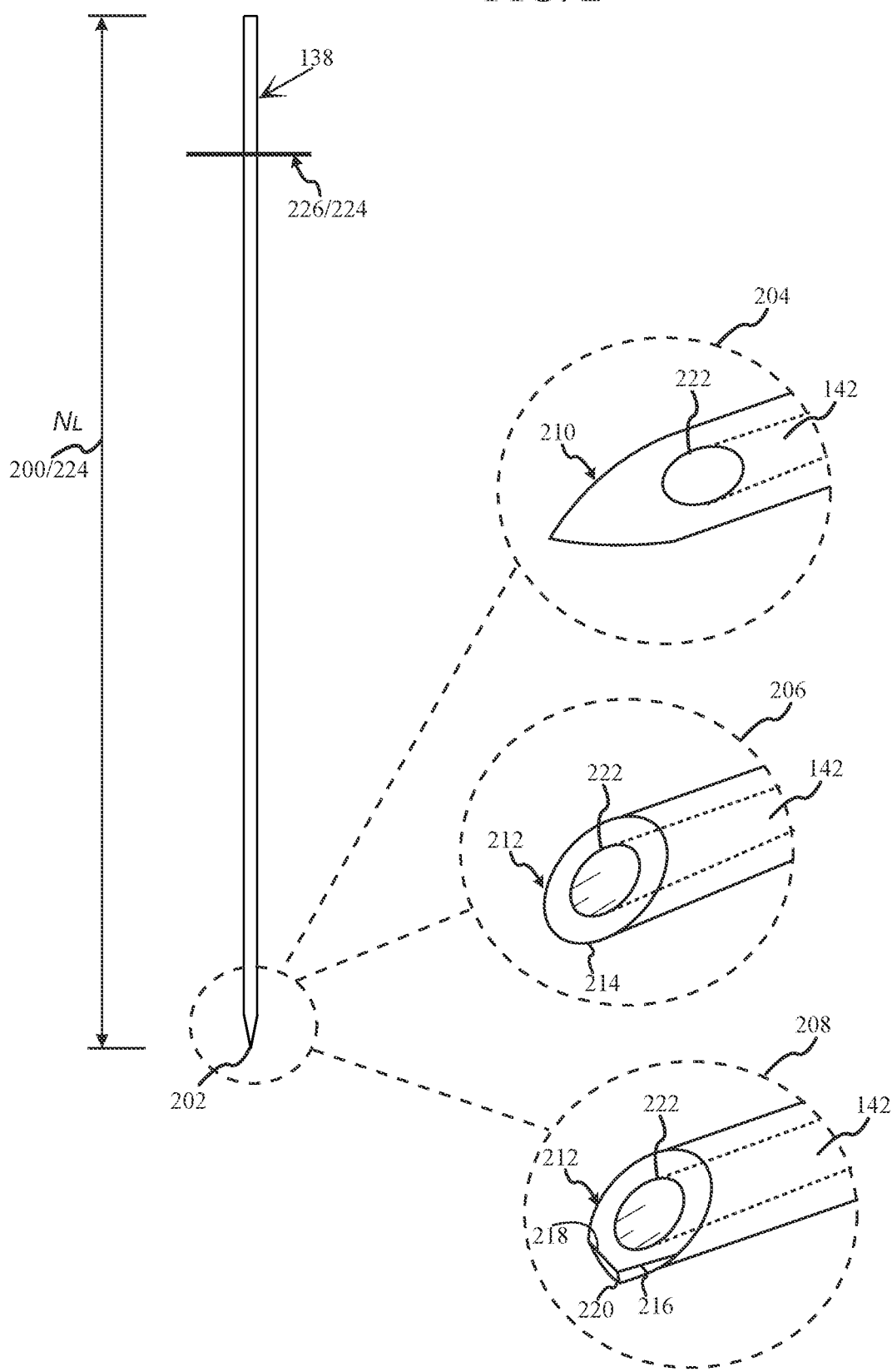
FIG. 2 conceptually illustrates the extractor needle as first shown in FIG. 1 with optional variations of the distal end in accordance with at various embodiment of the present invention.

FIG. 2 is presented to illustrate one or more embodiments of the extraction needle 138. More specifically, the extraction needle 138 has been conceptually rendered without the accompanying tubing 146 leading to the fluid reservoir 144, or the cannula 102. The extraction needle 138 may therefore be appreciated to have a length NL 200. The penetrating/puncturing/cutting distal end 202 has been rendered with various options shown in enlarged sections 204, 206 and 208.

Moreover, for at least one embodiment the extraction needle 138 has a pointed distal end 210 as shown in enlarged section 204, the point structured and arranged to penetrate the surface 118 (not shown in FIG. 2). For at least one alternative embodiment, the extraction needle 138 has a sharpened tip 212 providing at least one cutting edge 214. In other words, the end of the needle may be cleaved or shaved at an angle to provide at least one sharpened edge 214.

Further still, as shown in enlarged section 208 for at least one embodiment the end of extraction needle 138 has been shaped along three planes to provide at least two sharp edges 216 and 218 which advantageously serve as cutting edges to ease passage of the extraction needle 138 through the surface 118, as oppose to the more traditional needle with a single point that punctures and then stretches/pushes the tissues out of the way and in so doing may inflict ripping of the tissues comprising the surface 118. Additional edge 220 is also sharp, but depending on the alignment of the planes may not be as advantageously significant as sharp edges 216 and 218.

The opening 222 proximate to the distal end 200 is in fluid connection with the internal passage 142 of the extraction needle 138 which is ultimately connected to the fluid reservoir 144, shown in FIG. 1. For at least one embodiment the opening 210 may be fitted with a screen Not shown). Of course, an additional screen or filter may be incorporated in the fluid conduit leading to the fluid reservoir 144.

It will also be understood and appreciated that SFACAF 100 is intended for use for the safe and efficient withdrawal of amniotic fluid with minimal risk to the fetus and mother mammal. Moreover, for at least one embodiment, the SFACAF 100 incorporates a limiter 224, structured and arranged to limit the penetration depth of the extraction needle 138 beyond the surface 118. This limiter may be functionally or structurally achieved in a variety of different ways.

As noted above, for at least one embodiment, the extraction needle 138 itself may be preselected to have a specific length 200 chosen with respect to the length 132 of the cannula 102, such that the when the operator has inserted the extraction needle 138 into the central passage 112, the distal tip 202 of the needle only protrudes beyond the attachment end 104 by a known distance that has been predetermined to be safe for the fetus. Moreover, for at least one embodiment the limiter 224 is the extraction needle 138 length 200.

For yet another embodiment, the extraction needle 138 or the cannula 102 may have limiter 224 in the form of a blocker structured and arranged to block the passage of the extraction needle 138 beyond a certain point. For at least one embodiment, such a blocker is a cross bar 226, bulge, or other element affixed to the extraction needle 138 such that the extraction needle 138 cannot be inserted into the central passage 112 beyond a certain point. In other words, the limiter 224, aka cross bar 226, will catch across the open end of the central passage 112, thereby preventing further insertion of the extraction needle 138. Moreover, for at least one embodiment the limiter 224 is the cross bar 226.

The central passage 112 may also have blocker disposed therein, such as a dedicated channel or groove (not shown) to receive the extraction needle 138 and which will bind with the wall of the extraction needle 138 as the width of the extraction needle 138 increases. In an alternative embodiment, the channel may have a rotating or sliding element, such as a cam, which moves to achieve an ever increasingly tight friction grip with the extraction needle 138 as the extraction needle 138 is inserted, the movement or rotation preselected so as to insure a maximum insertion point of the extraction needle 138.

For still yet another embodiment, the limiter 224 may again be related to the length of the extraction needle 138, however for this particular embodiment the length of the needle is such that the distal end 200 of the extraction needle 138 does not extend beyond the attachment end 104. Rather, as a result of the suction force generated within the hollow chamber 110 and the upwelling of the tissues of the surface 118 into the concentric opening 106 of the attachment end 104, for at least some embodiments the central portion 122 of the surface will also rise into the central passage 112, and the central portion 122 is essentially presented to, and penetrated by, the distal end 200 of the extraction needle 138 even though the extraction needle has not extended past the attachment end 104.

For at least one embodiment, to assist with such upwelling of the central portion 122 of the tissue, a partial vacuum may also be established within the hollow chamber 110, such as by disposing a suction device within the central passage 112 or at least partially over the external end 108 of the cannula 102.

Figure 3:
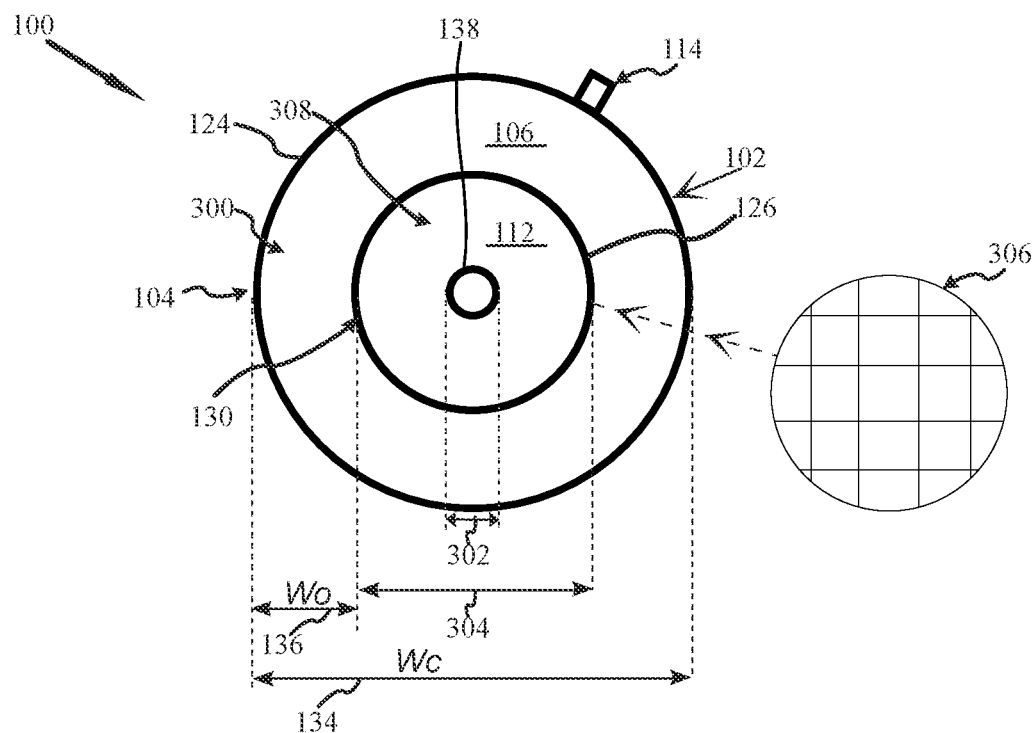
FIG. 3 is an end view of the attachment end of the system for aseptic collection of mammalian amniotic fluid shown in FIGS. 1A and 1B in accordance with at least one embodiment of the present invention.

FIG. 3 presents an end on view of the attachment end 104 of the core elements of SFACAF 100, namely the cannula 102 with the extraction needle 138 disposed within the central passage 112. With respect to FIG. 3, the relative size and circumferential disposition of the concentric opening 106 provided by the distal ends 128 and 130 of the outer wall 124 and inner wall 126 may also be appreciated as the suction cavity 300 which advantageously achieves the suctional attachment of the attachment end 104 to the surface 118 (not shown in FIG. 3).

As may be appreciated from FIG. 3, the relative size of the extraction needle 138 (more specifically the cross section 302 of the extraction needle 138) is quite small in comparison to the cross section 304 defined by the inner wall 126, which defines the central portion 122 of the amnio surface 118. As such, SFACAF 100 permits a user to not only isolate and clean the central portion 122 of the surface 118, but the operator is also afforded the ability to select where in the central portion 122 he or she wishes to direct the extraction needle 138.

For at least one embodiment a screen 306 may be provided over or slightly within the open end 308 of the central passage 112 proximate to the attachment end 104. It will also be understood and appreciated, that for at least one embodiment, at least a portion of the screen mesh is of an appropriate size to accommodate the passage of the extraction needle 138.

Figure 4A:
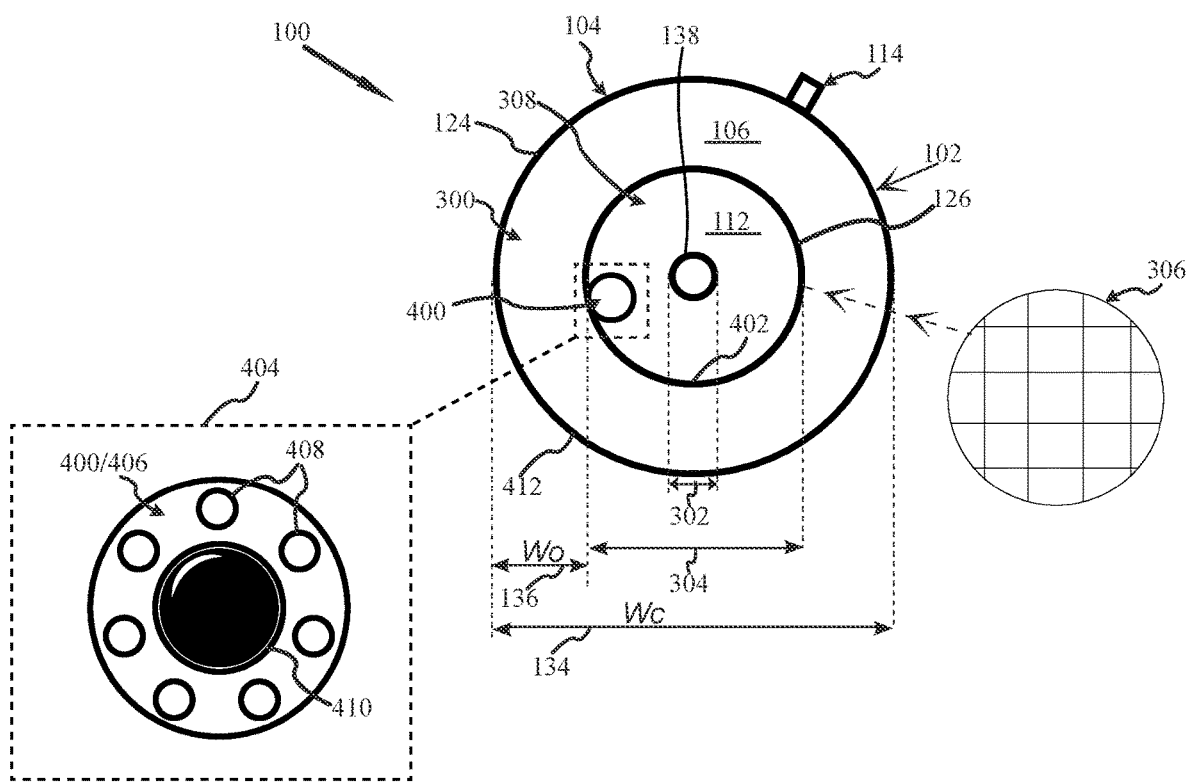
FIG. 4A is a longitudinal cut through view of the system for aseptic collection of mammalian amniotic fluid further including a borescope disposed in the central passage in accordance with at least one embodiment of the present invention.
Figure 4B:
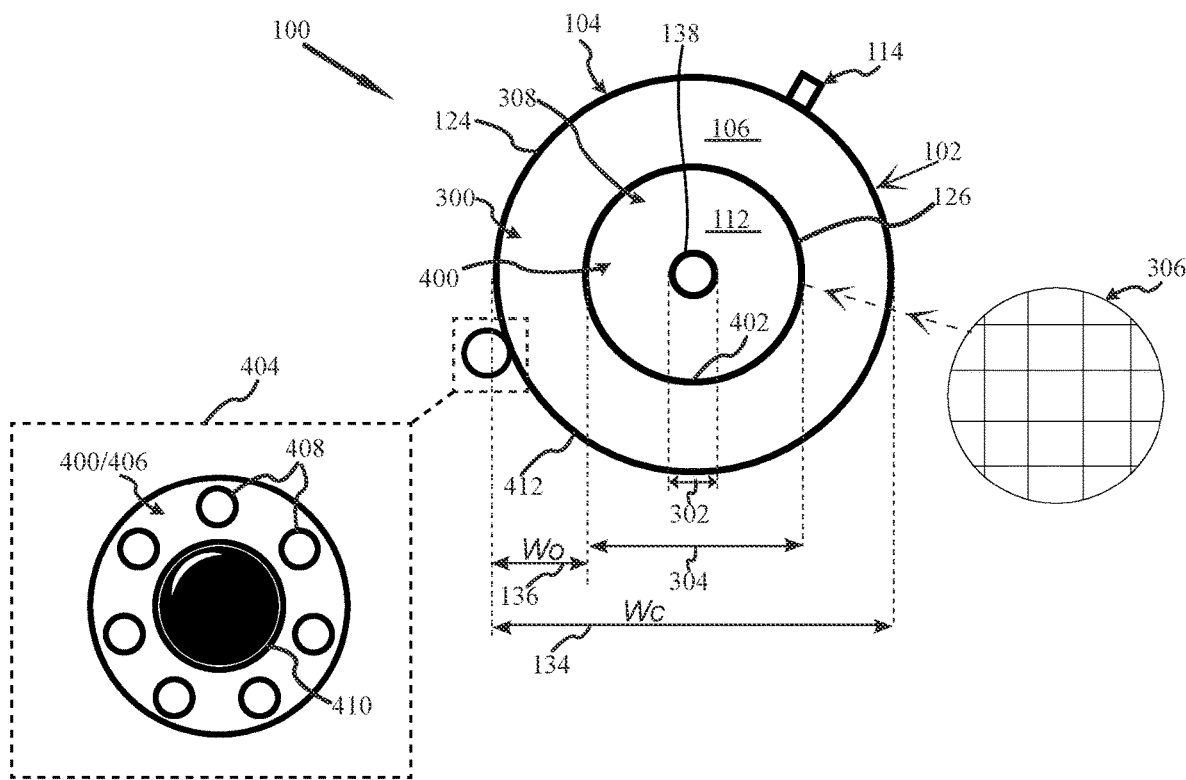
FIG. 4B is a longitudinal cut through view of the system for aseptic collection of mammalian amniotic fluid further including a borescope disposed upon the external surface of the cannula in accordance with at least one embodiment of the present invention.

As shown in FIG. 4A-4B, for at least one embodiment, to further aid in the extraction process permitted by SFACAF 100, for at least one embodiment a borescope 400 to aid the operator in visualizing the placement of the extraction needle 138. It will be appreciated that the borescope may provide light to the area proximate to the surface 118 as well as video/optical imaging of the surface 118, as well as potentially at least some of the subsurface area.

For at least one embodiment as shown in FIG. 4A, the borescope 400 may be disposed within the central passage 112 as a distinct and separate element, just as the extraction needle 138. For at least one alternative embodiment, the borescope 400 may be joined to an inside surface 402 of the central passage 112, such that it is present and able to illuminate and/or provide the operator with visual awareness of the central portion 122 without requiring the operator to manipulate or otherwise stabilize the borescope 400.

FIG. 4AA presents an end view of the attachment end 104 conceptually illustrating the location of the borescope 400 within the central passage 112 (loosely disposed or fixedly attached to the inside surface 402), and an enlarged view in dotted relief 404 showing the end 406 of the borescope 400 and specifically at least one Light Emitting Diode, e.g., LED 408 and camera 410. In varying embodiments, the camera 410 may indeed be a miniaturized camera system, however the camera 410 may also be the distal end of an optical fiber that is coupled to a camera external to the cannula 102.

For yet another embodiment as shown in FIG. 4B, the borescope 400 is joined to an outside surface 412, such as the outer wall 124, of the cannula 102 proximate to the concentric opening 106 of the attachment end 104. FIG. 4BB presents an end view of the attachment end 104 for the borescope 400 placement shown in FIG. 4B.

Indeed, in varying embodiments, even multiple borescopes 400 may be provided to provide the operator with multiple views of the extraction process.

As noted above, for at least one embodiment the cannula 102 is a double walled structure. For at least one alternative embodiment the cannula 102 is at least a triple walled structure. Moreover, as shown in FIG. 5A and FIG. 5B (showing a cutaway and external view substantially paralleling FIGS. 1A and 1B), the hollow chamber 110 is a first hollow chamber 500 and the cannula 102 includes a second hollow chamber 502 that is disposed about the first hollow chamber 500. The first hollow chamber 500 provides first concentric opening 106 and the second hollow chamber 502 provides a second concentric opening 504.

As is shown, there is at least one vent 506 interconnecting the first hollow chamber 500 with the second hollow chamber 502. As such, the port 114 permits at least a partial suction to be established in both the first hollow chamber 500 and the second hollow chamber 502 to suctionally attach the attachment end 104 to the surface 118.

The use of multiple hollow chambers may be desired for some embodiments as the additional inner walls subdividing an otherwise large concentric opening 106 into a plurality of concentric openings may permit a greater suction force to be used for attachment without undue stress upon the tissues of the surface 118.

It will be understood and appreciated that the optional placement locations for a bore scope 400 as described above with respect to FIGS. 4A-4BB are equally adaptable to embodiments of the cannula 102 having two or more hollow chambers 110, e.g., first hollow chamber 500 and the second hollow chamber 502.

In addition to the system for SFACAF 100, and more specifically the cannula 102, the elements of the present invention and above description may be summarized to set forth at least one method for collecting mammalian amniotic fluid with the use SFACAF 100. It will be appreciated that the method as presented above, and summarized below, need not be performed in the order in which it is herein described, but that this description is merely exemplary of one embodiment for one method of collecting mammalian amniotic fluid with the use SFACAF 100.

In general, the method 600 will commence with the providing a cannula 102 as has been set forth and described above with respect to the drawings and FIGS. 1-4BB, block 602 More specifically, for at least one embodiment of the method, the cannula 102 is appreciated to have an attachment end 104 and opposite thereto an external end 108. The attachment end 104 provides at least one concentric opening 106 to at least one hollow chamber 110 disposed about a central passage 112 extending from the attachment end 104 to the external end 108. The cannula 102 further has at least one port 114 is disposed adjacent to the external end 108 of the cannula 100, the port structured and arranged for attachment to a suction system 116, the port thereby structured and arranged to permit at least a partial suction to be established within the at least one hollow chamber 110 about the central passage 112.

The method 600 proceeds with the user disposing the attachment end 104 of the cannula 102 through the birth canal to seat upon a tissue surface 118 within a pregnant mammal, block 604.

A suction is then developed within the at least one hollow chamber 110, block 606. This suction draws at least a portion of the tissue surface 118 into the at least one concentric opening 106 of the at least one hollow chamber 110 to temporarily attach and seal the at least one concentric opening 106 of the cannula 102 to the tissue surface 118.

Method 600 continues by disposing the extraction needle 138 through the central passage 112 of the cannula 102 and through the central portion 122 of the tissue surface 118, block 608.

With the extraction needle 138 now disposed through the central portion 122 of the tissue surface 118, amniotic fluid is now extracted from below the central portion 122 of the tissue surface 118 through the extraction needle 138, block 610.

Following the extraction of amniotic fluid, method 600 continues with the removing the extraction needle 138. In some applications of method 600 upon extraction of the needle 138 no treatment or redress of the tissue of the surface 118 may be necessary. Of course, it will be understood and appreciated that the surface may be sutured, glued, fused, bandaged, or otherwise repaired as may be deemed appropriate, to seal the seal the central portion 122 of the tissue surface 118, optional block 612.

Changes may be made in the above methods, systems and structures without departing from the scope hereof. It should thus be noted that the matter contained in the above description and/or shown in the accompanying drawings should be interpreted as illustrative and not in a limiting sense. Indeed, many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A system for aseptic collection of mammalian amniotic fluid, comprising:
   a cannula having an attachment end and external end, the attachment end providing a concentric opening to a hollow chamber disposed about a central passage, the hollow chamber having a port disposed adjacent to the external end, the port structured and arranged to permit at least a partial suction to be established within the hollow chamber, the attachment end thereby suctionally attached to a surface when the attachment end is disposed upon the surface;
   the hollow chamber is a first hollow chamber, the cannula including a second hollow chamber disposed about the first hollow chamber, with at least one vent interconnecting the first hollow chamber with the second hollow chamber, the port permitting at least a partial suction to be established in both the first hollow chamber and the second hollow chamber to suctionally attach the attachment end to the surface;
   the central passage providing access to a central portion of the surface surrounded by the concentric opening of the hollow chamber; and
   an extraction needle to be disposed within the central passage of the cannula and presented to the central portion of the surface, the extraction needle structured and arranged to puncture the central portion of the surface and extract amniotic fluid there beneath.

2. The system of claim 1, further including a fluid reservoir in fluid connection with the extraction needle.

3. The system of claim 1, wherein the hollow chamber is a cylindrical hollow chamber.

4. The system of claim 1, further providing a borescope within the central passage.

5. The system of claim 1, further providing a borescope joined to an outside surface of the cannula proximate to the concentric opening.

6. The system of claim 1, further providing a borescope joined to an inside surface of the central chamber proximate to the concentric opening.

7. The system of claim 1, wherein the hollow chamber is a first hollow chamber, the cannula including a second hollow chamber disposed about the first hollow chamber, with at least one vent interconnecting the first hollow chamber with the second hollow chamber, the port permitting at least a partial suction to be established in both the first hollow chamber and the second hollow chamber to suctionally attach the attachment end to the surface.

8. The system of claim 1, wherein the surface is an amniotic fluid sack.

9. The system of claim 1, wherein the cannula has a length of about 12 to 24 inches.

10. The system of claim 1, wherein the cannula has a width of about 1 to 2 inches.

11. The system of claim 1, wherein the concentric opening has a width of about 0.25 inch.

12. A system for aseptic collection of mammalian amniotic fluid, comprising:

a cannula having an attachment end and opposite thereto an external end with an open central passage passing therebetween;

a first hollow chamber disposed about the central passage and providing a first concentric opening proximate to the attachment end;

a second hollow chamber disposed about the first hollow chamber and providing a second concentric opening proximate to the attachment end;

at least one vent between the first hollow chamber and the second hollow chamber;

a suction port disposed in an outer wall of the cannula proximate to the external end, the suction port in communication with the second hollow chamber and structured and arranged to permit at least a partial suction to be established within the first hollow chamber and the second hollow chamber, the attachment end thereby suctionally attached to a surface when the attachment end is disposed upon the surface.

13. The system of claim 12, further including a fluid reservoir in fluid connection with the extraction needle.

14. The system of claim 12, further providing a borescope within the central passage.

15. The system of claim 12, further providing a borescope joined to an outside surface of the cannula proximate to the concentric opening.

16. The system of claim 12, further providing a borescope joined to an inside surface of the central chamber proximate to the concentric opening.

17. The system of claim 12, wherein the surface is an amniotic fluid sack.

18. The system of claim 12, wherein the cannula has a length of 12 to 24 inches.

19. The system of claim 12, wherein the cannula has a width of 1 to 2 inches.

20. The system of claim 12, wherein the concentric opening has a width of about 0.25 inch.

21. A system for aseptic collection of mammalian amniotic fluid, comprising:

a cannula having a double wall defining a hollow chamber about an open central passage, the cannula having an attachment end and an external end, the double wall further defining a concentric opening about the central passage at the attachment end;

a port disposed adjacent to the external end, the port structured and arranged to permit at least a partial suction to be established within the hollow chamber, the attachment end thereby suctionally attached to a surface when the attachment end is disposed upon the surface;

the central passage providing access to a central portion of the surface surrounded by the concentric opening of the hollow chamber; and an extraction needle to be disposed within the central passage of the cannula and presented to the central portion of the surface, the extraction needle structured and arranged to puncture the central portion of the surface and extract amniotic fluid there beneath.

22. The system of claim 21, further including a fluid reservoir in fluid connection with the extraction needle.

23. The system of claim 21, wherein the hollow chamber is a cylindrical hollow chamber.

24. The system of claim 21, further providing a borescope within the central passage.

25. The system of claim 21, further providing a borescope joined to an outside surface of the cannula proximate to the concentric opening.

26. The system of claim 21, further providing a borescope joined to an inside surface of the central chamber proximate to the concentric opening.

27. The system of claim 21, wherein the surface is an amniotic fluid sack.

28. The system of claim 21, wherein the cannula has a length of 12 to 24 inches.

29. The system of claim 21, wherein the cannula has a width of 1 to 2 inches.

30. The system of claim 21, wherein the concentric opening has a width of 0.25 inch.

31. A method for aseptic collection of mammalian amniotic fluid of a pregnant mammal having a birth canal, comprising:

providing a cannula, the cannula having;

an attachment end and external end, the attachment end providing at least one concentric opening to at least one hollow chamber disposed about a central passage, the at least one hollow chamber having a port disposed adjacent to the external end, the port structured and arranged to permit at least a partial suction to be established within the at least one hollow chamber, the attachment end thereby suctionally attached to a tissue surface when the attachment end is disposed upon the tissue surface;

the at least first hollow chamber disposed about a second hollow chamber, at least one vent interconnecting the first hollow chamber with the second hollow chamber, the port connecting to the first hollow chamber;

the central passage providing access to a central portion of the tissue surface surrounded by the concentric opening of the hollow chamber; and an extraction needle to be disposed within the central passage of the cannula and presented to the central portion of the tissue surface, the extraction needle structured and arranged to puncture the central portion of the tissue surface and extract amniotic fluid there beneath;

disposing the attachment end of the cannula through the birth canal to seat upon a tissue surface within the pregnant mammal;

developing a suction within the at least one hollow chamber, the suction drawing at least a portion of the tissue surface into the at least one concentric opening of the at least one hollow chamber to temporarily attach and seal the at least one concentric opening to the tissue surface;

disposing the extraction needle through the central passage of the cannula and through central portion of the tissue surface;

extracting amniotic fluid from below the central portion of the tissue surface through the extraction needle; and removing the extraction needle.

32. The method of claim 31, further including a fluid reservoir in fluid connection with the extraction needle.

33. The method of claim 31, further including washing the central portion of the tissue surface after attachment end is attached to the tissue surface.

34. The method of claim 31, further including sterilizing the central portion of the tissue surface after attachment end is attached to the tissue surface.

35. The method of claim 31, wherein the cannula provides at least a first hollow chamber disposed about a second hollow chamber, at least one vent interconnecting the first hollow chamber with the second hollow chamber, the port connecting to the first hollow chamber.

36. The method of claim 31, further including disposing a borescope within the central passage.

37. The method of claim 31, wherein the cannula further provides a borescope joined to an outside surface of the cannula proximate to the concentric opening.

38. The method of claim 31, wherein the cannula further provides a borescope joined to an inside surface of the central chamber proximate to the concentric opening.

39. The method of claim 31, wherein the surface is an amniotic fluid sack.

* * * * *